Figure 1:
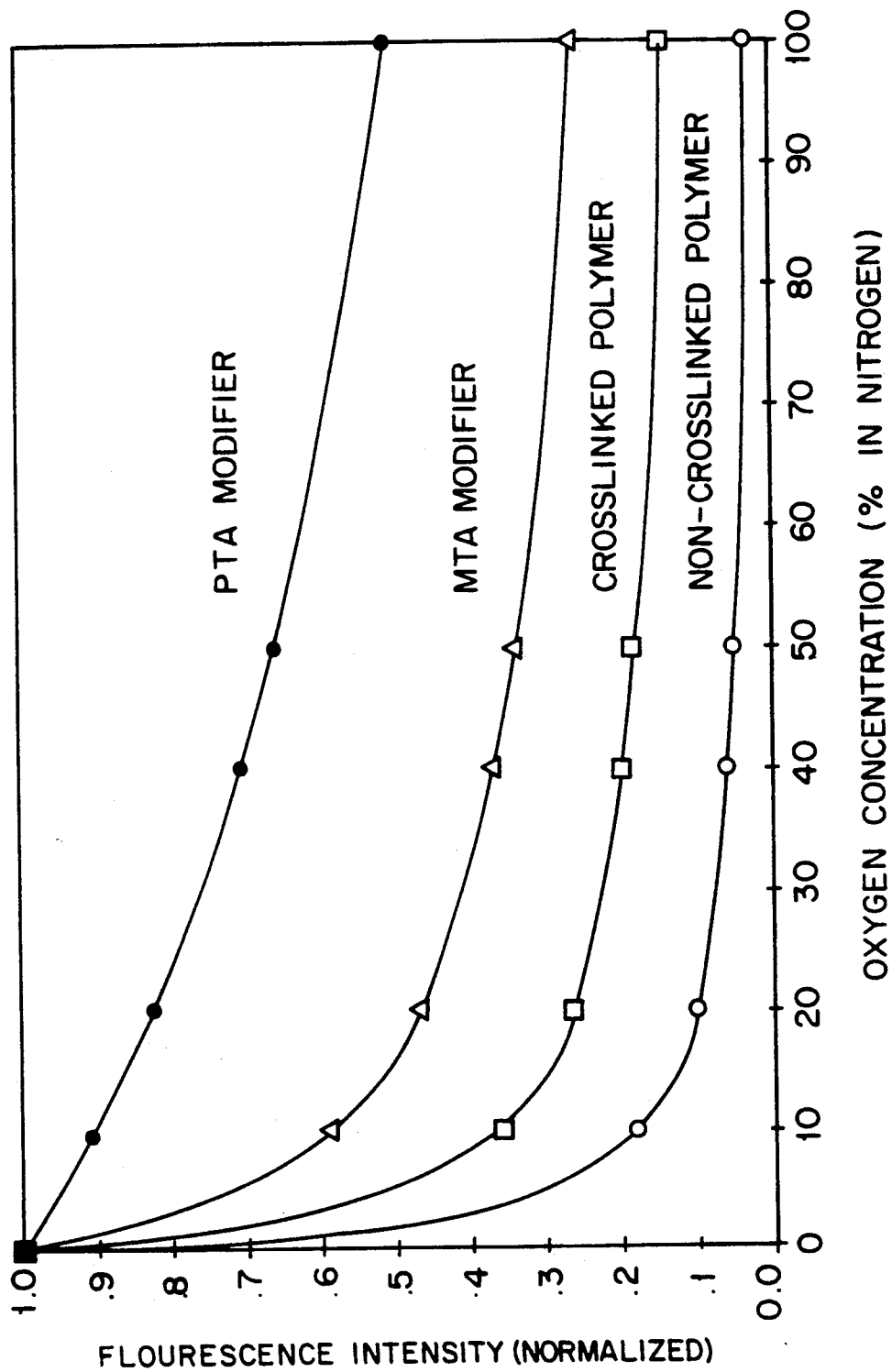

United States Patent [19]

Nauze et al.

[11] Patent Number: 5,194,391
[45] Date of Patent: Mar. 16, 1993

[54] CHEMICALLY SENSITIVE, DIMENSIONALLY-STABLE ORGANOSILICON MATERIAL COMPOSITION AND TECHNIQUES

[75] Inventors: Ganapati R. Nauze, Sunnyvale; Robert R. Holloway, Montara; Darlene J. Spira-Solomon, Stanford, all of Calif.

[73] Assignee: Hewlett-Packard Company, Palo Alto, Calif.

[21] Appl. No.: 720,983

[22] Filed: Jun. 25, 1991

Related U.S. Application Data

[62] Division of Ser. No. 259,015, Oct. 17, 1988, Pat. No. 5,057,277.

[51] Int. Cl.$^5$ ............... G01N 21/64; G01N 31/22
[52] U.S. Cl. .................. 436/166; 422/82.07; 422/82.08; 436/68; 436/136

[58] Field of Search ............... 422/56, 57, 68.1, 82.07, 422/82.08; 514/63; 436/68, 136, 166

[56] References Cited

U.S. PATENT DOCUMENTS 4,689,309  8/1987  Jones .................. 422/56 X

Primary Examiner—Jill A. Johnston

[57] ABSTRACT

A dimensionally-stable organosilicon material composition and method for producing the material composition including non-crosslinkable, continuous phase silicone with silica filler material dispersed therethrough, and having dissolved therein a variably-radiative material (e.g., ruthenium dye) responsive to the concentration of a selected analyte (e.g., oxygen), and the products of a reaction between water and a modifier material selected for establishing the sensitivity of said variably-radiative material to the selected analyte.

11 Claims, 1 Drawing Sheet

CHEMICALLY SENSITIVE, DIMENSIONALLY-STABLE ORGANOSILICON MATERIAL COMPOSITION AND TECHNIQUES

This is a division of application Ser. No. 07/259,015, filed Oct. 17, 1988, now U.S. Pat. No. 5,057,277.

TECHNICAL FIELD

The technical field addressed herein is that of chemically sensitive organosilicon material compositions and techniques, and particularly that of dimensionally-stable, chemically sensitive material compositions used in chemical sensing arrangements, as well as techniques for making such compositions.

BACKGROUND OF THE INVENTION

Organosilicon materials have been known for well over a century. However, their usefulness did not begin to be fully appreciated until the 1930's, and commercially viable techniques for silicon polymers were not identified until 1945. In that year, E. G. Rochow discovered the first "direct process" for synthesis of organochlorosilane. Since then, worldwide sales of organosilicons have risen into the billions of dollars, and, in every year, the field produces thousands of research papers.

However, not only organosilicon materials themselves but also compositions of organosilicon materials with a variety of other kinds of materials have become the focus of considerable attention in recent product development efforts. One kind of currently known organosilicon composition includes silicone in its continuous phase, with silica filler particles dispersed throughout its matrix as a filler to lend the continuous phase silicone strength and a level of dimensional stability. The silica particles within the silicone tend to align in chains, binding the continuous phase silicone by the effect of hydrogen bonding and endowing the continuous phase silicone in which the silica is dispersed with considerable dimensional stability. Continuous phase silicone is an oily fluid which readily flows under the influence of gravity. However, in a composition with sufficient amounts of silica, the silicone begins to acquire specific shape and form, and consequently at least a minimal level of dimensional stability. The continuous phase silicone thus becomes a matrix within which chains of silica are dispersed.

The introduction of certain other materials into the silicone matrix can destroy the malleability of the material composition, as occurs with the addition of modifier materials which react to produce cross-linkage between molecules of silicone. However, the introduction of dilute amounts of variably radiative materials into the silicone matrix itself does not destroy dimensional stability. The radiative characteristics (intensity and lifetime) of these materials vary in relationship to the concentration of a corresponding, selected analyte. Such radiative materials, dissolved into the silicone matrix and sensitive to analyte concentration, are particularly of interest in the development of gas detection arrangements. The radiative materials may be luminescent (i.e., photon producing). As is well known, luminescent materials are capable of radiation by phosphorescence, fluorescence, or chemiluminescence.

Accordingly it is an object of the invention herein to enable production of dimensionally-stable, malleable organosilicon material compositions for sensing concentrations of a selected analyte.

It is a further object of the invention that the dimensionally-stable, malleable organosilicon material composition developed be controllable in sensitivity with regard to analyte concentration.

It is an object of the invention that the dimensionally-stable organosilicon material composition of the invention remain dimensionally stable and malleable under broad ranges of environmental conditions with regard to temperature, pressure, and humidity.

It is another object of the invention that the dimensionally stable organosilicon material composition be both malleable and conveniently extrudable to facilitate ease of manufacture.

It is another object of the invention that the dimensionally stable organosilicon material composition exhibit selectable refractive indices to permit optical compatibility with optical fibers coupled to the material composition to facilitate communication therebetween.

It is a further object of the invention to develop a material composition which is suitable for use in the construction of sensitive instrumentation, such as medical diagnostic devices, which requires very close attention to precise manufacturing tolerances.

It is a further object of the invention to develop material compositions for use in oxygen detection arrangements insertable by catheter into the bloodstreams of living organisms.

It is a further object of the invention to produce a material composition which is dimensionally stable and variably radiative or luminescent in response to concentrations of the selected analyte.

It is a further object of the invention to develop a material composition which is substantially linearly, variably responsive to selected analyte concentrations over a predetermined range.

It is a further object of the invention to develop an organosilicon material composition for detecting analyte concentrations, which is not subject to the risk of cross-linkage between silicone molecules in the material composition.

It is an object of the invention to establish techniques for making organosilicon material compositions.

SUMMARY OF THE INVENTION

Accordingly, the invention herein is directed toward an analyte-concentration responsive, dimensionally-stable organosilicon material composition comprising continuous phase silicone; silica filler material distributed within the continuous phase silicone in an amount sufficient to establish dimensional stability for the continuous phase silicone; a selected concentration of variably radiative or luminescent (i.e., phosphorescent, chemiluminescent, or fluorescent) material having an affinity for silica filler material, and dissolved in said continuous phase silicone, the variably radiative material being responsive to the ambient concentration of a selected analyte, such as oxygen; and the dissolved reaction products of a controlled amount of selected modifier material with water, one of these reaction products being effective to control the sensitivity of the variably reactive material to analyte concentrations, the continuous phase silicone not being reactive with said selected modifier material.

The material composition of the invention can be optimized for analyte sensitivity. In other words, the material composition can be set to selected levels of sensitivity to a specific analyte by dissolving a predetermined amount of modifier material into the continuous phase silicone. Specifically, the sensitivity of the variably radiative material to an analyte depends upon the molecular environment of the variably radiative material. The modifier material, acting as an agent, provides an elution mechanism for effecting a specific distribution of the variably radiative material between the organosilicon and silica local matrix environments. The extent to which a given modifier agent is able to alter the distribution of the variably radiative material is a function of the relative polarity and affinity of the modifier and the radiative material for the respective organosilicon and silica matrix environments. For example, by dissolving a suitable modifier material (a hydrolizable modifier material, for example) in a solvent (sufficient ambient humidity or water vapor), particular polar products are produced, which compete with the selected radiative material for affinity to the silica. In the case of acetoxy or ethoxy silane modifiers hydrolized to produce, respectively, acetate or ethanol vapors, the vapors are believed to compete with the variably radiative material dissolved in the continuous phase silicone for optimal proximity with respect to the silica filler material dispersed therein. To the extent that sufficient amounts of variably radiative material are not in optimal proximity, the average sensitivity of the organosilicon material composition to analyte is diminished. Accordingly, the modifier material-derived reaction products establish a selected sensitivity level for the variably radiative material. Additionally, the index of refraction of the material composition is selectable by appropriately selecting its material constituents. In particular, the silicone material selected substantially contributes to the resultant index of refraction for the material composition as a whole. Other constituents of the material composition may also influence the index of refraction.

The continuous phase silicone into which the silica material is dispersed, and into which the variably radiative material and modifier material are dissolved, preferably, but not exhaustively, includes alkyl or aryl groups. These groups are nonreactive or inert with respect to the preferred triacetoxysilane modifier used in the material composition, thereby assuring the resultant material composition will be non-cross-linked and dimensionally stable over a wide variety of environmental conditions with regard to temperature and pressure. This silicone material preferably includes polydimethylsiloxane. The variably radiative material is preferably a dye taken from the category of tridiimine Ru (II) coordination complexes.

An organic solvent vehicle such as chloroform facilitates manufacture of the material composition and precise distribution of amounts of dye to be dissolved in the continuous phase silicone. To prepare the material composition indicated, a solution of selected vehicle is prepared containing the variably radiative material, and a second solution of the selected vehicle is prepared with a predetermined amount of silicone and an amount of modifier material corresponding to the extent of a desired modification of the sensitivity characteristic of the variably radiative material to analyte concentration. In particular, the material composition sensitivity characteristic without any modifier material may be typically linearly and highly sensitive for very low analyte concentrations. By selected increased amounts of modifier concentrations being included in the material composition of the invention, the sensitivity characteristic is modified controllably to have both increased sensitivity and enhanced linearity in a selected region of analyte concentrations of particular interest to the maker of the material composition. Simply stated, the slope and linearity of the sensitivity characteristic (i.e., the sensitivity of the material composition to specific ranges of analyte) is controllable.

Further, a sufficient amount of silica is added to the second solution to establish dimensional stability in the material composition once the vehicle is removed from the solution. Finally, the first and second solutions are combined by homogenizing the material composition. Typical mass ratios of modifier material to silicone are on the order of one over ten. The mass ratio of silicone to variably radiative material is on the order of one over 8,000. The variably luminescent material may include a ruthenium dye. The silicone may include polydimethylsiloxane. The selected modifier material is selected from the category of eluent-producing materials which can be used to selectively remove desired materials from close bonding to other materials with which they are weakly bonded. The eluent producing material may for example be an acetoxysilane. Other eluent producing materials are silanes such as for example carboxysilanes, alkoxysilanes, enoxysilanes, aminosilanes, or ketoxime silanes. Correspondingly, the eluent produced can be acetic acid, a carboxylic acid, an alkoxide, a ketone, or an oxime.

BRIEF DESCRIPTION OF THE DRAWING

The drawing shows normalized sensitivity characteristic curves with respect to oxygen concentration for selected organosilicon material compositions including a selected variably radiative material suspended in the material composition.

DETAILED DESCRIPTION OF A PREFERRED MODE OF THE INVENTION

The material composition according to the invention includes primarily continuous phase silicone material, frequently referred to as a silicone "matrix". The mass concentration of the material composition is for example on the order of 80% continuous phase silicone (for example, PSAR 148 or PSAR 157, available from Huels America). Dispersed within the silicone matrix are preferably particles of silica filler material (e.g., L-90 "Cab-O-Sil" available from Cabot Corporation), comprising about 10% of the mass concentration of the material composition. The silica filler material particles are preferably spherical and on the order of 0.024 microns in diameter and are dispersed throughout the silicone matrix by conducting a suitable mixing operation upon the material composition. A selected modifier material, such as phenyl triacetoxysilane (PTA) or methyl triacetoxysilane (MTA) is dissolved in the continuous phase silicone and contributes another 10% mass concentration to the material composition. Additionally included in the material composition is a selected radiative material, such as luminescent ruthenium dye, for example, which responds in degree of radiativity to the concentration of a particular analyte (e.g., oxygen) to be sensed. The percent by mass of this variably radiative material is on the order of 0.1%. The chemical structure of the continuous phase silicone includes covalently bonded chains of silicon and oxygen atoms surrounded at the ends and sides by "R" functional groups including preferably several phenyl or alkyl groups, or comparable groups, none of which is reactive with the selected modifier material. If the "R" functional groups of the silicone are reactive with the modifier material, crosslinkage of the silicone molecules may result, rendering the resultant material composition rubbery and non-malleable. This effectively eliminates extrudability of the material composition. By ensuring the presence of phenyl, alkyl, or similar functional groups which are nonreactive with the particular modifier material used, malleability of the material composition is ensured.

The silica filler material particles have a hydrogen bond affinity for each other and adjacent silicone molecules, causing adjacent silica particles to align end-to-end, in the form of a chain lending strength and increased dimensional stability to the silicone matrix in which the silica filler particles are dispersed. The use of an approximately 10% mass proportional amount of silica ensures adequate dimensional stability for the material composition of the invention herein. Greater amounts of silica increase the stability of the material composition, but with too much silica, the material composition tends to become undesirably gritty in texture.

A preferred variably radiative material is the oxygen sensitive luminescent material, e.g., a ruthenium (II) dye. Under illumination, the ruthenium dye is excited, and it luminesces at an intensity and for a lifetime which varies in relationship to local matrix oxygen concentration. Ruthenium dye molecules have an affinity for silica and distribute themselves over and about the surface of the silica particles, at a particular separation distance at which they tend to luminesce according to a particular characteristic curve depending upon analyte concentration. The preferred modifier, phenyl triacetoxysilane, introduced under suitable conditions of ambient humidity, insures the production of acetic acid in proportion to the amount of the modifier material used. The modifier material elutes the ruthenium dye from the silica chains to the organosilicon environment, which results in a relative decrease in analyte sensitivity for the material composition and a substantially linear intensity and lifetime response over desired analyte concentration ranges, as will be discussed in reference to the drawing. This effect is believed to arise from competition between the acetic acid and the ruthenium dye molecules for proximity to the surface of the silica particles. This competition tends to displace some of the ruthenium dye molecules from their established silica environment, resulting in an average diminished level of luminescence with increased amounts of acetic acid.

The drawing shows sensitivity characteristics, i.e., curves of radiative intensity normalized with respect to an arbitrary intensity level, for a range of different material compositions. The lower-most curve shows normalized intensity with respect to oxygen concentration for a material composition containing uncrosslinked silicone, silica particles dispersed therein, and a selected amount of luminescent material. The particular material composition includes no modifier material, and its characteristic curve is labeled "NON-CROSSLINKED POLYMER". The oxygen sensitivity of this material composition is greater than that of any other material composition depicted in the Drawing. The presence of even a very small concentration of oxygen substantially reduces the luminescence. However, the characteristic curve is notably non-linear over a variety of oxygen concentration regions. This is undesirable and makes this particular material composition generally uninteresting for certain detection arrangements. Sensitivity can be modified by using a crosslinked polymer, as shown in the curve labeled "CROSSLINKED POLYMER". However, as already indicated, the effect of polymer crosslinkage renders the material composition non-malleable and non-extrudable.

The intensity characteristic curves "PTA MODIFIER" and "MTA MODIFIER" (i.e., respectively, based upon PSAR 148 continuous phase silicone, with a predetermined concentration of either PTA or MTA modifier) further reduce sensitivity to oxygen. The linearity of these curves is greatest for "PSAR-PTA" in the higher (i.e., 40-80%) oxygen concentration range; and for "PSAR-MTA", in the lower (i.e., 20-40%) oxygen concentration range.

EXAMPLE

The material composition of the invention preferably includes ruthenium dye, i.e., tris (4,7-diphenyl-1,10-phenanthroline) ruthenium II dichloride, prepared in the following way. First, a solvent system is made by dissolving 13.5 grams of lithium chloride in 100 milliliters of ethylene glycol. Then, 10 milliliters of the solvent are used to dissolve 0.49 gram diphenylphenanthroline in a 50-milliliter round-bottom flask fitted with a stirrer and reflux condenser. The resultant material is heated to a bath temperature of about 138 degrees Celsius. Then, 0.12 gram of ruthenium trichloride trihydrate are added. After two hours of heating, the composition is cooled, and repeated amounts of water, first in the amount of 30 milliliter, then in successive 100 milliliter amounts, are poured over the dye material, until a suitably developed precipitate appears. Thereafter, the material is poured over a Buechner funnel to permit it to be vacuum aspirated to a dry state. The material is then further dried overnight in a warm oven.

The crude yield according to this procedure is about 0.55 gram, substantially as theoretically predicted. The primary impurity in this material is non-reactive diphenyl phenanthroline, which can be removed by dissolving the material composition in ethanol, and then precipitating the material composition in water, and finally refrigerating the resultant dye. The remaining amounts of ethanol can be removed by rotary evaporation, and then chilling the material, permitting the dye to recrystallize. The entire procedure can be repeated as many times as desired to remove the diphenylphenanthroline impurity to a desired minimal level. The resultant dye material is crystalline and becomes increasingly red and less white-flaked with increased purity. Once the dye material is sufficiently pure, it is dissolved to the extent of 0.03676 gram in two-hundred milliliters of chloroform ($CHCl_3$).

After the variably radiative dye material has been prepared as indicated above, 0.92 gram of PSAR 148 silicone (from Huels America) and 0.13 gram of modified material, e.g. phenyl triacetoxysilane (PTA), are dissolved in about four milliliters of chloroform in a 50 milliliter, wide-mouth test tube. Next, 0.13 grams of L-90 "Cab-O-Sil" silica from Cabot Corporation is added and washed into the solution with a Pasteur pipette. Then, 5.2 milliliters of the ruthenium dye/chloroform solution is added to provide an adsorbed coating of dye on the dispersed silica particles. The resulting material can be suitably homogenized with a Brinkmann homogenizer, to enable establishment of silica filler material particle chain structures to strengthen the continuous phase silicone. The amount of silica determines the stiffness of the material composition, which preferably has the consistency of a paste. The resultant material composition can be used with chloroform solvent suspended therein or evaporated therefrom.

Methyl triacetoxysilane (MTA) can be employed in lieu of PTA as the selected modifier material. Further, PSAR 157 silicone can be used in lieu of PSAR 148 silicone, to obtain a higher refractive index (1.57 versus 1.48) for matching different kinds of glass or optical fiber in actual detector arrangements.

The organosilicon material composition according to the invention is permeable to selected analytes, such as oxygen, carbon dioxide, ammonia, and water vapor, for example. Continuous phase silicone is known to be hydrophobic; however, water in its vapor or gaseous state can permeate the silicone matrix without much difficulty. Depending upon the particular radiative material dissolved into the silicone matrix, different kinds of analytes or gaseous concentrations can act to quench the radiativity of the material composition, which is either inherent to the material (chemiluminescence) or generated in response to illumination from an external source (fluorescence or phosphorescence).

Accordingly, the material composition invented can be made by preparing a solution of a selected vehicle, e.g., chloroform, into which a variably radiative material, e.g., ruthenium dye, is dissolved to radiate in relationship to the concentration of a selected analyte, e.g., oxygen. The amount of variably radiative material to be added is sufficient to enable the selected analyte to be sensed. Another solution of a selected vehicle is prepared, into which a predetermined amount of silicone is dissolved with an amount of modifier material corresponding to the extent of desired sensitivity modification of the variably radiative material selected to sense analyte concentrations. Without any modifier material, maximum sensitivity to analyte is achieved, albeit without any assurance of linearity in the intensity characteristic as a function of oxygen concentration, over any appreciable range in concentration. Addition of a predetermined amount of modifier material has the effect of modifying the sensitivity characteristic of the variably radiative material, as well as the resultant material composition, to the extent desired, in correspondence to the amount of modifier material added. This has the result of establishing a desired relationship between relative intensity of lifetime and oxygen concentration, which relationship exhibits substantial linearity over desired oxygen concentration ranges, thereby being particularly suitable for chemical detection, especially with regard to oxygen as an analyte. The selected amount of modifier accordingly establishes a predetermined range of luminescence in the material composition. The amount of silica added is sufficient to establish dimensional stability for the material composition upon removal from solution.

The kind of silicone employed with the invention is non-reactive with the particular modifier material selected, to prevent crosslinkage of silicone molecules, which would eliminate the malleability of the material. Accordingly, the silicone used must have functional groups which are non-reactive with the particular modifier material. Such non-reactive functional groups may include alkyl or aryl, for example. These are non-reactive with the modifier material of choice, phenyl triacetoxysilane.

The description above illustrates one form of how the invention can be implemented. A range of changes and modifications will readily be apparent to those ordinarily skilled in the art. These changes and modifications are to be considered within the scope of this invention.

What is claimed is:

1. A method of preparing a material composition having a sensing ability for analytes permeable to the material composition, said sensing ability dependent upon a concentration of the analytes, comprising the steps of:
    preparing a solution of a solvent vehicle;
    adding a variably radiative material to said solution effective for radiating in relationship to the concentration of the analytes;
    adding modifier material for effecting a desired modification in the relationship of said variably radiative material to the concentration of the analytes;
    adding silicone to said solution, wherein said silicone is not reactive to and does not crosslink with said modifier material; and
    adding silica to said solution to establish dimensional stability for said material composition upon removal from solution.

2. The method according to claim 1 comprising the further step of homogenizing said solution.

3. The method according to claim 1 comprising the further step of removing said selected vehicle from said material composition.

4. The method according to claim 1 wherein the mass ratios of modifier material to silicone and silica to silicone are each on the order of one (1) over ten (10).

5. The method according to claim 1 wherein the mass ratio of silicone to variably radiative material is on the order of 8,000 over one (1).

6. A method for preparing a variably-radiative, dimensionally stable organosilicon material composition for sensing oxygen concentrations, comprising the steps of:
    (1) dissolving silicone in a solvent vehicle;
    (2) dissolving a selected modifier material in said selected vehicle, for effecting a desired relationship between radiativity and oxygen concentration in said material composition;
    (3) adding a sufficient amount of silica to said solvent vehicle to establish dimensional stability for said material composition; and
    (4) adding a sufficient amount of a selected oxygen-sensitive, variably radiative material to said solvent vehicle to enable oxygen sensing.

7. A method of preparing a variably luminescent, dimensionally stable organosilicon material composition for sensing oxygen concentration, comprising the steps of:
    (1) dissolving a predetermined amount of silicone in chloroform with a selected amount of a modifier material to establish a predetermined range of luminescence in said material composition;
    (2) adding a sufficient amount of silica particles dimensionally to stabilize the material composition; and
    (3) adding a sufficient amount of oxygen-sensitive, variably luminescent material to permit sensing of oxygen concentration.

8. The method according to claim 7 wherein said variably luminescent material includes a ruthenium dye.

9. The method according to claim 7 wherein said silicone includes polydimethylsiloxane.

10. The method according to claim 7 wherein said modifier material is a silane.

11. The method according to claim 10 wherein said silane is a triacetoxysilane.

* * * * *

UNITED STATES PATENT AND TRADEMARK OFFICE
CERTIFICATE OF CORRECTION

PATENT NO. : 5,194,391
DATED : March 16, 1993
INVENTOR(S) : Ganapati R. Mauze et al.

It is certified that error appears in the above-identified patent and that said Letters Patent is hereby corrected as shown below:

On the front page of the patent, in field [75] change first inventor's name from "Ganapati R. Nauze" to --Ganapati R. Mauze--. Also Item [19]: should read --Mauze--.

Signed and Sealed this

Twenty-third Day of November, 1993

Attest:

BRUCE LEHMAN

Attesting Officer

Commissioner of Patents and Trademarks